(12) United States Patent
Sohn et al.

(10) Patent No.: US 8,986,956 B2
(45) Date of Patent: Mar. 24, 2015

(54) METHOD FOR PRODUCING HUMAN EPIDERMAL GROWTH FACTOR IN LARGE VOLUME FROM YEAST

(75) Inventors: Jung Hoon Sohn, Daejeon (KR); Jung Hoon Bae, Daejeon (KR); Mi Jin Kim, Daejeon (KR); Hyun Jin Kim, Daejeon (KR); Soon Ho Park, Daejeon (KR); Kwang Mook Lim, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/883,264

(22) PCT Filed: Nov. 4, 2011

(86) PCT No.: PCT/KR2011/008390
§ 371 (c)(1),
(2), (4) Date: Jul. 16, 2013

(87) PCT Pub. No.: WO2012/060666
PCT Pub. Date: May 10, 2012

(65) Prior Publication Data
US 2013/0323785 A1    Dec. 5, 2013

(30) Foreign Application Priority Data
Nov. 4, 2010  (KR) .................. 10-2010-0109441

(51) Int. Cl.
| C12P 21/04 | (2006.01) |
| C12N 1/16 | (2006.01) |
| C12N 15/09 | (2006.01) |
| C07H 21/04 | (2006.01) |
| C07K 14/485 | (2006.01) |
| C12N 15/81 | (2006.01) |
| C12R 1/645 | (2006.01) |

(52) U.S. Cl.
CPC .............. C07K 14/485 (2013.01); C12N 15/81 (2013.01); C12R 1/645 (2013.01)
USPC ................ 435/69.9; 435/255.1; 435/255.2; 435/255.4; 435/255.5; 435/255.6; 435/255.7; 435/320.1; 536/23.4

(58) Field of Classification Search
None
See application file for complete search history.

(56) References Cited

U.S. PATENT DOCUMENTS

| 5,037,760 A | 8/1991 | Smith et al. |
| 5,212,058 A | 5/1993 | Baker et al. |
| 5,362,644 A | 11/1994 | Boquet et al. |
| 5,536,637 A | 7/1996 | Jacobs |
| 5,547,871 A | 8/1996 | Black et al. |
| 5,563,046 A | 10/1996 | Mascarenhas et al. |
| 5,712,113 A | 1/1998 | Chung et al. |
| 5,952,171 A | 9/1999 | McCarthy et al. |
| 6,136,569 A | 10/2000 | Baker et al. |
| 6,150,098 A | 11/2000 | Zhang et al. |
| 6,228,590 B1 | 5/2001 | Baker |
| 6,541,619 B1 | 4/2003 | Park et al. |
| 6,548,633 B1 | 4/2003 | Edwards et al. |
| 7,029,842 B2 | 4/2006 | Duffner et al. |
| 2002/0127557 A1 | 9/2002 | Tan et al. |
| 2002/0160482 A1 | 10/2002 | Abrahmsen et al. |
| 2003/0108908 A1* | 6/2003 | Rhee et al. .................. 435/6 |
| 2004/0110939 A1 | 6/2004 | Dumas Milne Edwards et al. |
| 2007/0275385 A1 | 11/2007 | Sohn et al. |
| 2009/0181425 A1 | 7/2009 | Sohn et al. |
| 2010/0159465 A1* | 6/2010 | Sohn et al. .................. 435/6 |

FOREIGN PATENT DOCUMENTS

| EP | 1170366 A1 | 1/2002 |
| EP | 0907727 B1 | 10/2002 |
| EP | 1790661 A2 | 5/2007 |
| JP | 2003-530106 A | 10/2003 |
| JP | 2008-263975 A | 6/2008 |
| WO | 97/40146 A1 | 10/1997 |
| WO | 98/21348 A1 | 5/1998 |
| WO | 99/49028 A1 | 9/1999 |
| WO | 00/52133 A2 | 9/2000 |
| WO | 01/00806 A2 | 1/2001 |
| WO | 01/77315 A1 | 10/2001 |

(Continued)

OTHER PUBLICATIONS

Joo-Hyung Heo et at., "Purification of Recombinant Human Epidermal Growth Factor Secreted form the Methylotrophic Yeast Hansenula polymorpha", Protein Expression and Purification vol. 24, pp. 117-122 (2002).

(Continued)

*Primary Examiner* — Marianne P Allen
(74) *Attorney, Agent, or Firm* — Joseph R. Baker, Jr.; Gavrilovich, Dodd & Lindsey LLP

(57) ABSTRACT

The present invention relates to a method for producing hEGF (human epidermal growth factor) which has the same activity as the wild form, in high concentration and with a high degree of purity. More specifically, the invention relates to an hEGF expression vector comprising a nucleic acid sequence coding for the polypeptide of sequence number 14; a host cell in which the expression vector has been genetically transformed; and a method for producing hEGF, comprising a step in which the expression vector is created and is genetically transformed in yeast from which the KEX1 gene is lacking. Using the method of the present invention, it is possible to produce a large volume of human derived EGF which has the same size and activity as human derived EGF, and this EGF can be used in various ways such as in medicine and cosmetics.

14 Claims, 7 Drawing Sheets

(56) References Cited

FOREIGN PATENT DOCUMENTS

| WO | 02/057423 A2 | 7/2002 |
| WO | 02/072821 A2 | 9/2002 |
| WO | 2005/038024 A1 | 4/2005 |
| WO | 2005/068658 A1 | 7/2005 |
| WO | 2007/012188 A1 | 2/2007 |
| WO | 2007/015178 A2 | 2/2007 |
| WO | 2007/035930 A2 | 3/2007 |

OTHER PUBLICATIONS

GenBank Accession No. Np_011620 (Dec. 9, 2009).
GenBank Accession No. 1IVO_C(Sep. 24, 2008).
Baldari, C., et al., "Differential stability of human interleukin 1 beta fragments expressed in yeast," Protein Eng. 1:433-437, JRL Press Limited, England (1987).
Broekhuijsen, M.P. et al., "Secretion of heterologous proteins by *Aspergillus niger*: Production of active human interleukin-6 in a protease-deficient mutant by KEX2-like processing of a glucoamylase-hIL6 fusion protein", J Biotechnol. 31:135-145, Elsevier Science Publishers B.V., Netherlands (Nov. 1993).
Contreras, R. et al., "Efficient KEX2-like Processing of a Glucoamylase-interleukin-6 Fusion Protein by *Aspergillus nidulans* and Secretion of Mature Interleukin-6", Bio/Technology (N.Y.) 9:378-381, Nature Pub. Co., United States (Apr. 1991), abstract only.
Crosier, P.S., et al., "In Situ Hybridization Screen in Zebrafish for the Selection of Genes Encoding Secreted Proteins," Developmental Dynamics 222:637-644, Wiley-Liss, Inc., United States (2001).
Dorner, A.J. et al., "Overexpression of GRP78 mitigates stress induction of glucose regulated proteins and blocks secretion of selective proteins in Chinese hamster ovary cells", The EMBO Journal 11:1563-1571, Oxford University Press, England (1992).
Dorner, A.J., et al., "Reduction of Endogenous GRP78 Levels Improves Secretion of a Heterologous Protein in CHO Cells," Molecular and Cellular Biology 8:4063-4070, American Society for Microbiology, United States (1988).
Downing, K.J., et al., "*Staphylococcus aureus* nuclease is a useful secretion reporter for mycobacteria", Gene 239:293-299, Elscience Science B.V., Netherlands (1999).
Eckert, M.R. et al., "Quality and authenticity of heterologous proteins synthesized in yeast", Curr. Opin. Biotechnol., 7:525-530, Current Biology Ltd., England (Oct. 1996).
Ferguson, D.A., et al ., "Selective Identification of Secreted and Transmembrane Breast Cancer Markers using *Escherichia coli* Ampicillin Secretion Trap," Cancer Res 65:8209-8217, American Association for Cancer Research, United States (2005).
Galliciotti, G., et al., "Signal-sequence Trap in Mammalian and Yeast Cells: A Comparison," J. Membrane Biol. 183:175-182, Springer-Verlag, United States (2001).
Goo, J.H., et al., "Selection of *Arabidopsis* genes encoding secreted and plasma membrane proteins," Plant Molecular Biology 41: 415-423, Kluwer Academic Publishers, Netherlands (1999), abstract only.
Gouka, R.J ., et al., "Efficient production of secreted proteins by *Aspergillus*: progress, limitations and prospects," Appl. Microbial. Biotechnol. 47:1-11, Springer-Verlag, Germany (Jan. 1997).
Harmsen, M.M., et al., "Overexpression of binding protein and disruption of the PMR1 gene synergistically stimulate secretion of bovine prochymosin but not plant Thaumatin in yeast," Appl Microbiol Biotechnol. 46:365-370, Springer-VerlaQ, Germany (Nov. 1996).
Hayano, T., et al., "Protein disulfide isomerase mutant lacking its isomerase activity accelerates protein folding in the cell," FEBS Lett. 377:505-511, Federation of European Biochemical Societies, Netherlands (Dec. 1995).
Hsu, T . -A ., et al., "Effects of Co-expressing Chaperone BiP on Functional Antibody Production in the Baculovirus System," Protein Expr Purif. 5 : 595-603, Academic Press, Inc. , United States (Dec. 1994).
Jacobs, K.A., et al., "A genetic selection for isolating cDNAs encoding secreted proteins" Gene 198:289-296, Elsevier Science BV, Netherlands (1997).
Jeenes, D.J., et al., "A truncated glucoamylase gene fusion for heterologous protein secretion from *Aspergillus niger*," FEMS Microbial Lett., 107: 267-272, Federation of European Microbiological Societies, Netherlands (Mar. 1993), abstract only.
Kjeldsen, T., et al., "Prepro-Leaders Lacking N-linked Glycosylation for Secretory Expression in the Yeast *Saccharomyces cerevisiae*," Protein Expr Purif. 14:309-316 , Academic Press, United States (Dec. 1998).
Kjeldsen, T., et al., "Synthetic Leaders with Potential BiP Binding Mediate NPL19 High-Yield Secretion of Correctly Folded Insulin Precursors from *Saccharomyces cerevisiae*", Protein Expr Purif. 9:331-336, Academic Press., United States (Apr. 1997).
Klein, R.D., et al., "Selection for genes encoding secreted proteins and receptors ," Proc. Natl. Acad. Sci. USA 93: 7108-7113 , National Academy of Sciences, United States (Jul. 1996).
Langlella, P. et al., "Heterologous protein secretion in *Lactococcus lactis*: a novel antigen delivery system", Braz. J. Med. Biol. Res. 32:191-198, Associacao Brasileira de Divulgacao Cientifica, Brazil (1999).
Lee, J. et al., "Novel Secretion System of a Recombinant *Saccharomyces cerevisiae* Using an N-terminus Residue of Human IL-1B as Secretion Enhancer", Biotechnol. Prog. 15:884-890, American Chemical Society and American Institute of Chemical Engineers, United States (1999).
Lim, E.M. et al., "Identification of *Mycobacterum tuberculosis* DNA Sequences Encoding Exported Proteins by Using phoA Gene Fusions", J. Bacteriol. 177:59-65, American Society for Microbiology, United States (Jan. 1995).
MacConaill, L.E. et al., "Investigation of Protein Export in *Bifidobacterium breve* UCC2003", Appl. Environ. Microbiol. 69:6994-7001, American Society for Microbiology, United States (Dec. 2003).
Makrides, S.C., "Strategies for Achieving High-Level Expression of Genes in *Escherichia coli*", Microbiological Reviews 60:512-538, American Society for Microbiology, United States (1996).
Monteoliva, L, et al., "Large-Scale Identification of Putative Exported Proteins in *Candida albicans* by Genetic Selection", Eukaryotic Cell, 1:514-525, American Society for Microbiology, United States (Aug. 2002).
Muesch, A. et al., "A novel pathway for secretory proteins?" TIBS 15:86-88, Elsevier Science Publishers Ltd., United Kingdom (Mar. 1990).
Nakajima, H. et al., "Expression of an 87-kD-B-1, 3-Glucanase of *Bacillus circulans* IAM1165 in *Saccharomyces cerevisiae* by Low-temperature Incubation", Biosci. Biotech. Biochem. 57:2039-2042, Japan Society for Bioscience, Biotechnology, and Agrochemistry, Japan (1993).
Roberts, I.N. et al., "Heterologous gene expression in *Aspergillus niger*. a glucoamylase-porcine pancreatic prophospholipase A2 fusion protein is secreted and processed to yield mature enzyme", Gene 122:155-161, Elsevier Science Publishers B.V., Netherlands (Dec. 1992), abstract only.
Robinson, A.S. et al., "Protein Disulfide Isomerase Overexpression Increases Secretion of Foreign Proteins in *Saccharomyces cerevisiae*," Bio/Technology (NY) 12:381-384, Nature Pub. Co., United States (Apr. 1994), abstract only.
Robinson, A.S. et al., "Reduction of BiP Levels Decreases Heterologous Protein Secretion in *Saccharomyces cerevisiae*", J. Biol. Chem. 271:10017-10022, American Society for Biochemistry and Molecular Biology, United States (1996).
Sagt, C.M.J. et al., "Introduction of an N-Glycosylation Site Increases Secretion of Heterologous Proteins in Yeasts", Applied and Environmental Microbiology 66:4940-4944, American Society for Microbiology, United States (2000).
Schultz, L.D. et al., "Using Molecular Genetics to Improve the Production of Recombinant Proteins by the Yeast *Saccharomyces cerevisiae*," Ann NY Acad Sci, 721:148-157, New York Academy of Sciences, United States (May 1994).
Sohn, J. et al., "Human IL-2 secretion, TFP SEQ ID No. 29", in WO 2007/015178, A2, Accession No. AEX30558 (2007).

(56) References Cited

OTHER PUBLICATIONS

Sohn, J. et al., "Human IL-2 secretion, TFP SEQ ID No. 175", in WO 2007/015178, A2, Accession No. AEX30704 (2007).

Surpili, M.J. et al., "A yeast-based model system for cloning secreted and membrane proteins", An Acad Bras Cienc 74:599-608, Academia Brasileira De Ciencias, Brasil (2002).

Takahashi, S. et al., "Function of the prosequence for in vivo folding and secretion of active *Rhizopus oryzae* lipase in *Saccharomyces cerevisiae*", Appl Microbiol Biotechnol., 55:454-462, Springer Verlag, Germany (May 2001).

Tan, N.S. et al., "Engeineering a novel secretion signal for cross-host recombinant protein expression", Protein Eng., 15:337-345, Oxford University Press, England (2002).

Wang, H. et al., "Molecular characterization of a PDI-related gene prpA in *Aspergillus niger* var. awamori," Curr Genet 37:57-64, Springer-Verlag, Germany (Jan. 2000).

Ward, P.P. et al., "A system for production of commercial quantities of human lactoferrin: a broad spectrum natural antibiotic", Bio/Technology (NY), 13:498-503, Nature Pub Co., United States (May 1995), abstract only.

Ward, M. et al., "Improved Production of Chymosin in *Aspergillus* by Expression as a Glucoamylase-Chymosin Fusion", Bio/Technology 8:435-440, Nature Pub Co., United States (1990), abstract only.

\* cited by examiner

MKLSTVLLSAGLASTTLAAPVNTTTEDETAQIPAEAVIGYLDLEGDFDVA

VLPFSNSTNNGLLFINTTIASIAAKEEGVAASASAGLALDKR VINSLGWP
MFαpro-pro                                Linker FEDEDGDDEYATEETIS HHHHHH GDDDK NSDSECPLSHDGYCLHDGVCM
HL Peptide        6His   EK    hEGF

YIEALDKYACNCVVGYIGERCQYRDLKWWELR

SEQUENCE LISTING

```
<160> NUMBER OF SEQ ID NOS: 19

<210> SEQ ID NO 1
<211> LENGTH: 21
<212> TYPE: DNA
<213> ORGANISM: Artificial Sequence
<220> FEATURE:
<223> OTHER INFORMATION: GAL100 primer

<400> SEQUENCE: 1
gtatatggtg gtaatgccat g                                             21

<210> SEQ ID NO 2
<211> LENGTH: 24
<212> TYPE: DNA
<213> ORGANISM: Artificial Sequence
<220> FEATURE:
<223> OTHER INFORMATION: DDK-R Primer

<400> SEQUENCE: 2
cttatcgtca tcgtcaccgt ggtg                                          24

<210> SEQ ID NO 3
<211> LENGTH: 37
<212> TYPE: DNA
<213> ORGANISM: Artificial Sequence
<220> FEATURE:
<223> OTHER INFORMATION: H410 Primer

<400> SEQUENCE: 3
ggtgacgatg acgataagaa ctccgactcc gagtgtc                            37

<210> SEQ ID NO 4
<211> LENGTH: 50
<212> TYPE: DNA
<213> ORGANISM: Artificial Sequence
<220> FEATURE:
<223> OTHER INFORMATION: GT40R Primer

<400> SEQUENCE: 4
gtcattatta aatatatata tatatatatt gtcactccgt tcaagtcgac              50

<210> SEQ ID NO 5
<211> LENGTH: 36
<212> TYPE: DNA
<213> ORGANISM: Artificial Sequence
<220> FEATURE:
<223> OTHER INFORMATION: H411 Primer

<400> SEQUENCE: 5
cactccgttc aagtcgactt actatcatct cagctc                             36

<210> SEQ ID NO 6
<211> LENGTH: 27
<212> TYPE: DNA
<213> ORGANISM: Artificial Sequence
<220> FEATURE:
<223> OTHER INFORMATION: H464

<400> SEQUENCE: 6
```

-continued gacgaattca tgttttacaa taggtgg                                         27

<210> SEQ ID NO 7
<211> LENGTH: 37
<212> TYPE: DNA
<213> ORGANISM: Artificial Sequence
<220> FEATURE:
<223> OTHER INFORMATION: H468 Primer

<400> SEQUENCE: 7
cgaccacacc cgtcctgtca tcttctaggt cttcgtc                              37

<210> SEQ ID NO 8
<211> LENGTH: 37
<212> TYPE: DNA
<213> ORGANISM: Artificial Sequence
<220> FEATURE:
<223> OTHER INFORMATION: H469 Primer

<400> SEQUENCE: 8
cgatgctgtc ggaatggaca gatatttcct ttgtcag                              37

<210> SEQ ID NO 9
<211> LENGTH: 30
<212> TYPE: DNA
<213> ORGANISM: Artificial Sequence
<220> FEATURE:
<223> OTHER INFORMATION: H467 Primer

<400> SEQUENCE: 9
agtctcgagt taagtagtaa tcataacatt                                      30

<210> SEQ ID NO 10
<211> LENGTH: 23
<212> TYPE: DNA
<213> ORGANISM: Artificial Sequence
<220> FEATURE:
<223> OTHER INFORMATION: TcF Primer

<400> SEQUENCE: 10
acaggacggg tgtggtcgcc atg                                             23

<210> SEQ ID NO 11
<211> LENGTH: 21
<212> TYPE: DNA
<213> ORGANISM: Artificial Sequence
<220> FEATURE:
<223> OTHER INFORMATION: U200R Primer

<400> SEQUENCE: 11
tgacccaatg cgtctcccatt g                                              21

<210> SEQ ID NO 12
<211> LENGTH: 24
<212> TYPE: DNA
<213> ORGANISM: Artificial Sequence
<220> FEATURE:
<223> OTHER INFORMATION: U200F Primer

<400> SEQUENCE: 12
gttaagccgc taaaggcatt atcc                                            24

<210> SEQ ID NO 13
<211> LENGTH: 23
<212> TYPE: DNA

<213> ORGANISM: Artificial Sequence
<220> FEATURE:
<223> OTHER INFORMATION: TcR Primer

<400> SEQUENCE: 13
gtccattccg acagcatcgc cag                                          23

<210> SEQ ID NO 14
<211> LENGTH: 25
<212> TYPE: PRT
<213> ORGANISM: Artificial Sequence
<220> FEATURE:
<223> OTHER INFORMATION: HL Peptide

<400> SEQUENCE: 14

Val Ile Asn Ser Leu Gly Trp Ala Phe Glu Asp Glu Asp Gly Asp
1               5                   10                  15

Glu Tyr Ala Thr Glu Glu Thr Leu Ser
            20                  25

<210> SEQ ID NO 15
<211> LENGTH: 53
<212> TYPE: PRT
<213> ORGANISM: Homo sapiens

<400> SEQUENCE: 15

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 16
<211> LENGTH: 5
<212> TYPE: PRT
<213> ORGANISM: Artificial Sequence
<220> FEATURE:
<223> OTHER INFORMATION: Enterokinase Recognition Sequence

<400> SEQUENCE: 16

Asp Asp Asp Asp Lys
1               5

<210> SEQ ID NO 17
<211> LENGTH: 79
<212> TYPE: PRT
<213> ORGANISM: Artificial Sequence
<220> FEATURE:
<223> OTHER INFORMATION: MF Alpha Pre-Pro Leader

<400> SEQUENCE: 17

Met Lys Leu Ser Thr Val Leu Leu Ser Ala Gly Leu Ala Ser Thr Thr
1               5                   10                  15

Leu Ala Ala Pro Val Asn Thr Thr Thr Glu Asp Glu Thr Ala Gln Ile
            20                  25                  30

Pro Ala Glu Ala Val Ile Gly Tyr Leu Asp Leu Glu Gly Asp Phe Asp
        35                  40                  45

Val Ala Val Leu Pro Phe Ser Asn Ser Thr Asn Asn Gly Leu Leu Phe
    50                  55                  60

```
Ile Asn Thr Thr Ile Ala Ser Ile Ala Ala Lys Glu Glu Gly Val
 65                  70                  75

<210> SEQ ID NO 18
<211> LENGTH: 13
<212> TYPE: PRT
<213> ORGANISM: Artificial Sequence
<220> FEATURE:
<223> OTHER INFORMATION: Linker Peptide

<400> SEQUENCE: 18

Ala Ala Ser Ala Ser Ala Gly Leu Ala Leu Asp Lys Arg
 1               5                  10

<210> SEQ ID NO 19
<211> LENGTH: 182
<212> TYPE: PRT
<213> ORGANISM: Artificial Sequence
<220> FEATURE:
<223> OTHER INFORMATION: hEGF fusion construct

<400> SEQUENCE: 19

Met Lys Leu Ser Thr Val Leu Leu Ser Ala Gly Leu Ala Ser Thr Thr
 1               5                  10                  15

Leu Ala Ala Pro Val Asn Thr Thr Glu Asp Glu Thr Ala Gln Ile
                 20                  25                  30

Pro Ala Glu Ala Val Ile Gly Tyr Leu Asp Leu Glu Gly Asp Phe Asp
             35                  40                  45

Val Ala Val Leu Pro Phe Ser Asn Ser Thr Asn Asn Gly Leu Leu Phe
         50                  55                  60

Ile Asn Thr Thr Ile Ala Ser Ile Ala Ala Lys Glu Glu Gly Val Ala
 65                  70                  75                  80

Ala Ser Ala Ser Ala Gly Leu Ala Leu Asp Lys Arg Val Ile Asn Ser
                 85                  90                  95

Leu Gly Trp Ala Phe Glu Asp Glu Asp Gly Asp Gly Asp Gly Tyr Ala Thr
            100                 105                 110

Glu Glu Thr Leu Ser His His His His His His Gly Asp Asp Asp Asp
            115                 120                 125

Lys Asn Ser Asp Ser Glu Cys Pro Leu Ser His Asp Gly Tyr Cys Leu
            130                 135                 140

His Asp Gly Val Cys Met Tyr Ile Glu Ala Leu Asp Lys Tyr Ala Cys
145                 150                 155                 160

Asn Cys Val Val Gly Tyr Ile Gly Glu Arg Cys Gln Tyr Arg Asp Leu
                165                 170                 175

Lys Trp Trp Glu Leu Arg
            180
```

METHOD FOR PRODUCING HUMAN EPIDERMAL GROWTH FACTOR IN LARGE VOLUME FROM YEAST

This application is a U.S. National Stage Application filed under 35 U.S.C. §371 and claims priority to International Application No. PCT/KR2011/008390, filed Nov. 4, 2011, which application claims priority under 35 U.S.C. §119 to Korean Application No. 10-2010-0109441, filed Nov. 4, 2010, the disclosures of which are incorporated herein by reference.

TECHNICAL FIELD

The present invention relates to a method for producing hEGF (human epidermal growth factor) which has the same activity as wild type in high concentration and high purity. Specifically, the present invention relates to hEGF expression vector comprising a nucleic acid sequence encoding the polypeptide of SEQ ID NO: 14, a host cell transfected with the expression vector, and a method for producing hEGF, comprising preparing the expression vector and transfecting the same to the KEX1 gene-deleted yeast.

BACKGROUND ART

EGF (Epidermal growth factor) is a polypeptide consisting of 53 amino acids, and first identified to be secreted from the submandibular gland of rats. Since then, in addition to the ability to stimulate the growth of skin cells of epithelium and epidermis in various tissues of the body, hEGF (human epidermal growth factor) has been known to promote the growth and differentiation of epithelial cells of the cornea and lung (Carpenter, G. Handbook of Experimental Pharmacology, 1981, 57, 89). Due to these features, the EGF has been developed and widely used as the wound medicine, and recently, is drawing attention as the raw material of functional cosmetics with proven anti-wrinkle and anti-aging effects (Brown, G. L, U.S. Pat. No. 5,618,544). Initially, EGF has limitation in productivity due to being extracted from human placenta and urine, but the productivity has been improved enough to be used as a cosmetic raw material as the recombinant hEGF production systems have been developed due to the development of genetic engineering techniques. Demand of hEGF is gradually increasing according to extending the scope of use, but hEGF has become a major factor raising the price of functional cosmetics due to the high production cost. Thus, in order to popularize functional cosmetics and expand the market of hEGF products, the issue of hEGF production cost must be solved.

The recombinant expression of the desired protein is widely used as a method for mass production of proteins for research, therapeutic, or other commercial purposes. In order to produce large quantities of recombinant proteins, various vectors and hosts are used, and typically a method using *E. coli* is widely used. Most of currently produced hEGF is produced by expressing a synthetic human EGF gene in *E. coli*, and the case of expression in yeast has been reported (Urdea, N. S. et al. P.N.A.S., 1983, 86, 7461; Korea Patent 1990-0022194). When expressed in *E. coli*, the gene is expressed in the form of fusion protein in combination with fibronectin collagen-binding domain (Ishikawa, T. et al., J. Biochem., 2001, 129, 627), amino terminus of swine growth factor (Xial, C J et al., J. Mol. Endocrinol., 1996, 16, 89) or a part of TrpE protein of *E. coli* (Allen, G, et al., J. Cell Sci. Suppl., 1985, 3, 29), or expressed simply by adding six histidine amino acids (Lee, J Y et al. Biotechnol. Appl. Biochem., 2000, 31, 245).

These methods provide a high protein expression level, but have the disadvantage of high cost due to necessities of the activation process in order to form the tertiary structure consisting of three cysteine bonds such as hEGF protein and activate to form a three-dimensional structure since the protein is expressed in the form of inactive inclusion body, and various stages of the purification process in order to obtain the hEGF with high purity.

Meanwhile, yeast *Saccharomyces cerevisiae*, which is a eukaryotic microorganism, is a GRAS (Generally Recognized As Safe) microorganism proven safe for humans, easy to modify genetically, and has various expression systems developed. In addition, it provides the advantages of performing the secretory function to secrete the proteins out of the cell when recombining the higher cell-derived proteins such as human proteins and post-translational modification of protein such as glycosylation. In order to produce the target protein through secretion, extracellular secretion is possible by artificial fusion of protein secretory signal and the target protein, and protein folding, disulfide bond formation and the addition process of sugar chain are progressing through the secretion process of protein. Therefore, it offers the advantage of producing the recombinant protein with biologically complete activity. It also can recover the biologically active proteins directly from the medium without breaking the cells, and is very economical because the refolding step is not required (Eckart and Bussineau, Curr. Opin. Biotechnol., 1996, 7, 525).

However, due to low productivity of the active form of EGF compared to the *E. coli*, the yeast *Saccharomyces cerevisiae* has not received attention as EGF-producing strain.

Accordingly, as the results of the efforts to produce the active hEGF in yeast with high concentration and high purity, the present inventors identified that, if expressing hEGF fused with HL (Hydrophilic domain) peptide having a specific amino acid sequence derived from VOA1 gene in KEX1 gene-deleted strains, hEGF with the same conformation and activity as wild type can be mass-produced, to complete the present invention.

DISCLOSURE

Technical Problem

The objective of the present invention is to provide a method for producing hEGF (human epidermal growth factor) which has the same activity with the wild type in high concentration and high purity.

Another objective of the present invention is to provide a hEGF expression vector, wherein the hEGF has the same conformation and activity as wild type.

Another objective of the present invention is to provide a host cell transfected with the hEGF expression vector.

Technical Solution

As an embodiment to achieve the objectives, the present invention provides a method for producing hEGF comprising i) preparing hEGF (human epidermal growth factor) expression vector comprising a nucleic acid sequence encoding a polypeptide of SEQ ID NO: 14; and ii) transfecting the expression vector of step i) to the KEX1 gene-deleted yeast.

The present invention, by transfecting hEGF expression vector comprising a nucleic acid sequence encoding the polypeptide of SEQ ID NO: 14 to the KEX1 gene-deleted yeast, allows the increased production of the hEGF with the same conformation and activity as the wild type by more than 5 times compared to the case of transfecting the hEGF expression vector without the above nucleic acid sequence to the wild type yeast.

Therefore, it is preferable that the hEGF produced in the above method, which has the same activity as the wild type, comprises an amino acid sequence of SEQ ID NO: 15.

The expression vector may further comprise a nucleic acid sequence encoding an affinity tag, or nucleic acid sequence encoding a protease recognition sequence, or both.

Addition of affinity tag to the vector may facilitate the purification of the product in the form of fusion of the polypeptide of SEQ ID NO: 14 and hEGF produced in the yeast. In addition, if the protease recognition sequence is added to the vector, the product in the form of fusion of purified polypeptide of SEQ ID NO: 14 and hEGF is treated with protease, and the polypeptide of SEQ ID NO:14 can be easily separated from hEGF.

As another embodiment, the present invention provides an hEGF expression vector which a nucleic acid sequence encoding the polypeptide of SEQ ID NO: 14 and a nucleic acid sequence encoding hEGF are operably linked to.

As another example, the present invention provides a host cell transfected with the vector.

Hereinafter, the present invention is described in detail.

hEGF has been drawing attention as a wound medicine or raw material of cosmetics for anti-wrinkle or anti-aging, but is limited in popular use due to difficulty of mass production and high production costs.

Hereupon, as an embodiment, the present invention provides a method for producing hEGF (human epidermal growth factor), which has the same activity as the wild type, in high concentration and high purity.

Specifically, the present invention provides a method for producing hEGF comprising i) preparing hEGF (human epidermal growth factor) expression vector comprising a nucleic acid sequence encoding the polypeptide of SEQ ID NO: 14; ii) transfecting the expression vector of step i) to the KEX1 gene-deleted yeast.

In a method for producing hEGF of the present invention, the step i) is to prepare the vector comprising a nucleic acid encoding the polypeptide of SEQ ID NO: 14 and a nucleic acid encoding hEGF.

The polypeptide of SEQ ID NO: 14 is derived from a gene encoding C-terminus deleted yeast VOA1 protein (YGR106c). It is a part of HL (Hydrophilic domain) peptide domain, which is composed of hydrophilic amino acids and has the highest charge, in the VOA1 protein domain.

As used herein, the term "polypeptide" refers to any chain or chains of two or more amino acids, but not to a specific length of the product. Therefore, any other terms used to indicate peptides, dipeptides, tripeptides, oligopeptides, proteins, amino acid chains, or chain or chains of two or more amino acids of the print or print are included in the definition of "polypeptide", and the term "polypeptide" can be used instead of, or interchangeably with any other terms. In addition, the term "polypeptide", although is not limited to, may include the product of modification after polypeptide expression such as glycosylation by the known protector/breaker, acetylation, phosphorylation, amidation, derivatization, proteolytic cutting, or in-spontaneous modification by amino acid. The polypeptide may be derived from natural biological sources or prepared by recombinant techniques, but not necessarily be translated from a given nucleic acid sequence. It can be generated in any manner, including chemical synthesis.

As used herein, the term "nucleic acid" refers to any one or more nucleic acid fragments present in the polynucleotide, for example, DNA or RNA fragments. The "polynucleotide", which includes plural nucleic acids as well as singular nucleic acid, refers to an isolated nucleic acid molecule or the product, for example, the messenger RNA (mRNA), virus-derived RNA or plasmid DNA (pDNA). Polynucleotide may comprise the conventional phosphodiester bond or a non-conventional bond (such as amide bond which is found in, for example, peptide nucleic acid (PNA)).

As used herein, the term "EGF" refers to epidermal growth factor with a function to stimulate the growth of skin cells of epithelium and epidermis in various tissues mainly of the human body.

In the present invention, the vector includes any functional vector in the selected host cell. As used herein, the term "vector" refers to a nucleic acid molecule which can carry another connected nucleic acid. "Plasmid", which is one type of the vector, refers to a circular double-stranded DNA loop which can connect additional DNA fragment within the same. A viral vector, which is another type of vector, can connect the additional DNA in the viral genome. Some vectors are capable of self-replication when introduced into a host cell (e.g., bacterial vectors having a replication origin and a mammalian episomal vector. Other vectors, when introduced into a host cell, are inserted into the host cell genome (e.g., non-episomal vectors of mammals) are replicated along with the host genome. Vectors in the present invention can direct the expression of a gene encoding the operably linked target protein, which are called "expression vectors". Typically, the expression vector in the use of recombinant DNA technology is in the form of a plasmid. In the present invention, the terms "plasmid" and "vector" can be used interchangeably to refer to plasmid, and the term of vector is used more commonly. However, the present invention also comprises other forms of expression vectors to perform the same functions, such as viral vectors (e.g., replication deficient retrovirus, adenovirus, and adenovirus-dependent virus). The expression of proteins in prokaryotes can be carried out by a vector comprising the constitutive or inducible promoter that directs the expression of the fusion protein of target protein and reporter protein. The yeast expression vector suitable for expression in a yeast strain includes pYepSec1 (Baldari et al., EMBO J, 5:229-234, 1987), pMFa (Kurjan et al., Cell 30:933-943, 1982), pJRY88 (Schultz et al., Gene 54:113-123, 1987), pYES2 (Invitrogen Corporation, San Diego, Calif.) and picZ (Invitrogen Corp., San Diego, CaL), but is not limited thereto.

Baculovirus can be used for expression in insect cells. Baculovirus can be used for protein expression in cultured insect cells comprising pAc series (Smith et al., Mol. Cell. Biol. 5:2156-2165, 1983) and pVL series (Lucklow et al., Virology 770:31-39, 1989). As another specific example, the host cell may be a mammalian cell and the vector may be a mammalian expression vector. An example of mammalian expression vector includes pCDM8 (Seed, Nature 329:840, 1987) and pMT2PC (Kaufman et al., EMBO J. 6: 187-195, 1987). When used in mammals, the control function of expression vector may be provided by viral regulatory sequences. For example, commonly used promoters are derived from polyoma, adenovirus 2, cytomegalovirus and SV40 (simian virus 40). Examples of other suitable expression system to apply to both prokaryotic and eukaryotic cells may be referred to MOLECULAR CLONING: A LABORATORY MANUAL (Sambrook et al., 2nd ed., Cold Spring Harbor Laboratory, Cold Spring Harbor Laboratory Press, Cold Spring Harbor, N.Y., 1989. The preferable vector includes plasmid, phage, cosmid, episome, viral particle or virus, and insertable DNA fragments (i.e., fragments which can be inserted into the host cell genome by homologous recombination), but is not limited thereto. The preferable viral particle includes adenovirus, baculovirus, parvovirus, herpesvirus, poxvirus, adenovirus-dependent virus, Semliki forest virus, vaccinia virus, and retroviruses, but is not limited thereto. The suitable expression vector includes pcDNA3 (Invitrogen) and pSVL (Pharmacia Biotech), but is not limited thereto. Other expression vectors include pSPORT™ vector, pGEM™ vector (Promega), pPROEX Vector™ (LTI, Bethesda, Md.), Bluescript™ vector (Stratagene), pQE™ vector (Qiagen), pSE420™ (Invitrogen) and pYES2™ (Invitrogen), but are not limited thereto.

As a specific example, the expression vector is a replicable DNA product operably linked to the appropriate control sequence which allows for nucleic acid sequence encoding hEGF to express hEGF protein effectively in an appropriate host.

As used herein, the term "operably linked" refers to a region of DNA being functionally connected to another region. For example, the promoter can be operably linked to the coding sequence to control the transcription of sequence. Amplification of the vector is related to the replication ability of the host usually caused by the replication origin and selectable gene to facilitate the recognition of the transformant, not to the expression of the control domain. The necessity of control sequences in the expression vector depends on the host type and the type of transfection method. In general, the control sequences include the transcription promoters, enhancers, selective operator sequences to control transcription, polyadenylation signals, an appropriate ribosome binding mRNA coding sequences, and sequences to control the termination of transcription and translation, but are not limited thereto. These control sequences are described, for example, in GENE EXPRESSION TECHNOLOGY: METHODS IN ENZYMOLOGY 185 (Goeddel, Academic Press, San Diego, Calif., 1990). The control sequences include the direct constitutive expression of the nucleic acid sequences in many types of host cells, and the direct expression of the nucleic acid sequence (e.g., tissue-specific control sequences) in some of the host cell. In addition, those skilled in the art can design the vector by considering factors such as the selection of the host cell to be transfected or desired protein expression levels.

For the objective of the present invention, it is preferable to use the vector capable of expressing in the yeast as the expression vector. In addition, the expression vector expresses hEGF, which preferably comprises the amino acid sequence represented by SEQ ID NO:15, as the target protein.

The expression vector can be introduced into the host cell to produce proteins or peptides, including fusion proteins or peptides encoded by the nucleic acid sequences described in the present invention. Preferably, the vector may comprise a promoter which is recognized by the host organism. The promoter sequence of the present invention may be originated from prokaryote, eukaryote or virus. Examples of prokaryote originated sequences include PR and PR promoter of bacteriophage lambda (The bacteriophage Lambda, Hershey, A. D., Ed., Cold Spring Harbor Press, Cold Spring Harbor, N.Y., 1973; Lambda II, Hendrix, R. W., Ed., Cold Spring Harbor Press, Cold Spring Harbor, N.Y., 1980); trp of *E. coli*, recA, heat shock and lacZ promoter, and SV40 early promoter (Benoist et al, Nature, 290:304-310, 1981). The appropriate promoter to yeast includes GAPDH, PGK, ADH, PHO5, GAL1 and GAL10, but is not limited thereto. Other promoter includes mouse mammary tumor virus (MMTV), long terminal repeat (LTR) of human immunodeficiency virus, maloney virus, cytomegalovirus immediate early promoter, Epstein Barr virus, Rous sarcoma virus, human actin, human myosin, human hemoglobin, human muscle creatine and human metallothionein, but is not limited thereto. Preferably, the vector may comprise additional control sequences. Representative examples of appropriate control sequences are Shine-Dalgano sequence of replicase gene of phage MS-2 and Shine-Dalgano sequence of c II of bacteriophage lambda.

Specifically, in a preferable example of the present invention, the promoter is GAL10.

In addition, the preferable expression vector can comprise an appropriate marker to select transfected host cells. The transfection of the host can be achieved by using one of the various techniques well-known in the art and the techniques described in the literature of Sambrook. Replication origin may be provided by the vector construction comprising foreign origin and may also be provided by the host cell chromosomal replication mechanism, of which the latter is satisfied if the vector is integrated into the host cell chromosome. On the other hand, instead of using a vector comprising viral replication origin, mammals may be transfected by means of co-transfection with a selectable marker and the target protein DNA.

The vector in the present invention also can comprise the nucleic acid sequence encoding the affinity tag in order to improve the effect of purification of the target protein. The affinity tag can be selected from the group consisting of GST, MBT, NuSA, thioredoxin, ubiquitin, FLAG, BAP, 6HIS, STREP, CBP, CBD, and S-tag, but is not limited thereto.

Specifically, in a preferable example of the present invention, the affinity tag is 6HIS.

In addition, by inserting a region that is recognized by a specific enzyme for separation of the target protein and protein secretory fusion partner, the efficient purification of the target protein of interest may be achieved. The preferable enzyme is protease. The protease recognition sequence can be selected from the group consisting of yeast kex2p, mammalian purine, Factor Xa, enterokinase, subtilisin, tobacco etch virus protease, thrombin, and ubiquitin hydrolase, but is not limited thereto. In a specific example of the present invention, the specific enzyme is enterokinase and the amino acid sequence recognized by enterokinase may include the sequence represented by SEQ ID NO: 16.

Therefore, the hEGF expression vector of the present invention may be the vector to which the nucleic acid sequence encoding the polypeptide of SEQ ID NO: 14, the nucleic acid sequence encoding the affinity tag, the nucleic acid sequence encoding protease recognition sequence, and the nucleic acid sequence encoding hEGF are sequentially and operably linked. In addition, the vector may further comprise nucleic acid sequence encoding MFα pre-pro leader peptide.

In an example of the present invention, the hEGF expression vector, to which the nucleic acid sequence encoding MFα pre-pro leader peptide, the nucleic acid sequence encoding the polypeptide of SEQ ID NO: 14, the nucleic acid sequence encoding the affinity tag, the nucleic acid sequence encoding protease recognition sequence, and the nucleic acid sequence encoding hEGF are sequentially and operably linked, was used. In addition, MFα pre-pro leader peptide (SEQ ID NO: 17) is linked to HL peptide using AASASAG-LALDKR sequence (SEQ ID NO: 18) as a linker peptide.

The preferable expression vector of the present invention is pYG-hlEGF illustrated in FIG. 1.

In a production method of hEGF of the present invention, the step ii) is to transfect the hEGF expression vector comprising a nucleic acid sequence encoding the polypeptide of SEQ ID NO: 14, which is prepared in step i), to the KEX1 gene-deleted yeast.

This step is to transfect the vector to the KEX1 gene deleted yeast in order to produce the hEGF with same activity as the wild type hEGF. In an example of the present invention, if the vector is transfected to the wild type yeast, the hEGF with different molecular weight from the wild type hEGF is produced, but if the vector is transfected to the KEX1 gene-deleted yeast, the hEGF with same molecular weight as the wild type hEGF is produced, which was identified to have the activity of original hEGF to regenerate the cells, and promote the collagen synthesis.

As used herein, the term "transfection" refers to the technology in the art to introduce foreign nucleic acid (e.g., DNA) into a host cell and includes calcium phosphate or calcium chloride co-precipitation, electroporation, DEAE-dextran mediated method or lipofection. Transfection to a host cell can be done in a proper manner well known in the art. For example, the method is well described in the literature such as Sambrook (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

It is known that the stable transfection to mammalian cells depends on the used expression vector and transfection technique and only some cells can have the foreign DNA inserted into their own genome. In order to screen and identify the inserts, gene encoding a selectable marker (e.g., antibiotic resistance) can be introduced into a host cell along with gene of interest. Various selection markers include G418, hygromycin and methotrexate which provide the drug resistance. Nucleic acid encoding a selectable marker can be introduced in connection to the vector such as nucleic acid encoding the target protein or another vector. Stably transfected cells can be identified by drug screening (for example, cells with selectable markers will survive and the others will die).

The host cell used in the present invention can be any host cell widely known in the art, and includes bacterial, fungus (for example, yeast), plan or animal (for example, mammal, insect) cell. The animal cell includes human, mouse, rat, rabbit, dog, cat, monkey and insect, and for example, includes CHO, COS 1, COS 7, BSC 1, BSC 40, BMT 10, and Sf9 cells.

Preferably, the host cell, in the present invention, is yeast, and more preferably, KEX1 gene-deleted yeast.

In order to delete the KEX1 gene, any gene deletion methods known in the art can be used without any limitation. In a more specific example of the present invention, it was carried out using the URA3 pop-out vector.

The yeast includes *candida, debaryomyces, hansenula, kluyveromyces, pichia, schizosaccharomyces, yarrowia, saccharomyces, schwanniomyces* or *arxula* species. The specific example of species includes *Candida utilis, Candida boidinii, Candida albicans, Kluyveromyces lactis, Pichia pastoris, Pichia stipitis, Schizosaccharomyces pombe, Saccharomyces cerevisiae, Hansenula polymorpha, Yarrowia lipolytica, Schwanniomyces occidentalis* or *Arxula adeninivorans*, but not limited thereto.

In addition, the production method of hEGF in the present invention can further comprise producing and secreting hEGF protein by fed batch fermentation and culture of transfected yeast. As a more specific example, the strains cultured in the minimal medium of 200 ml were inoculated to the fermentor of 5 L scale containing 1.8 L fermentation medium (2% glucose, 4% yeast extract, 1% peptone). When the glucose is completely exhausted, fermentation can proceed for 50 hours while adding feed medium (30% glucose, 30% galactose, 15% yeast extract) gradually by 2 g/L to 20 g/L per hour, depending on the growth of the cell.

The production method of hEGF in the present invention may also comprise the purification method well known in the art. For example, the host cell can be separated from the culture medium by the conventional chromatographic methods such as immunoaffinity chromatography, receptor affinity chromatography, hydrophobic interaction chromatography, lectin affinity chromatography, size-exclusion chromatography, cation or anion exchange chromatography, high performance liquid chromatography (HPLC) and reversed-phase HPLC. In addition, the desired protein, which is the fusion protein with specific tag, label, or chelate moiety, can be recognized by specific binding partners or drug and purified. The purified protein may be cut as desired part of protein, or it can remain as it is. The desired form of protein comprising additional amino acid may be produced from the cutting process by cutting the fusion protein.

In an example of the present invention, after transfecting hEGF expression vector comprising the nucleic acid sequence encoding the polypeptide of SEQ ID NO: 14 to the KEX1 gene-deleted yeast and culturing, if hEGF secreted from the yeast is separated and purified, the amount of secreted hEGF increases by approximately more than 5 times compared to the case of separating and purifying hEGF after transfecting hEGF expression vector without the nucleic acid sequence encoding polypeptide of SEQ ID NO: 14 to the wild type yeast (control group). In addition, although in the control group, hEGF having different molecular weight from the wild type hEGF, rather than the active hEGF was produced, in the production method of the present invention, a large amount of hEGF with same molecular weight as the wild type hEGF was produced, which was identified to exhibit the similar activity to promote the cell growth and collagen synthesis as the commercialized purified EGF (FIGS. 6 and 7). Therefore, the method of the present invention has an effect of mass-production of active hEGF.

As another embodiment, the present invention provides an hEGF expression vector which a nucleic acid sequence encoding the polypeptide of SEQ ID NO: 14 and a nucleic acid sequence encoding an hEGF are operably linked to.

The expression vector may comprise affinity tag and/or protease recognition sequence, wherein the preferable affinity tag is 6 histidines and the preferable protease recognition sequence is enterokinase recognition sequence, and more preferably, may be amino acid sequence represented by SEQ ID NO: 16.

The expression vector may additionally comprise the nucleic acid sequence encoding MFα pre-pro leader peptide as pre-pro leader, and preferably comprises the amino acid sequence set forth in SEQ ID NO: 17. In addition, in the vector of the present invention, the nucleic acid sequence encoding MFα pre-pro leader peptide is preferably linked to the nucleic acid sequence encoding HL (HydrophiLic domain) peptide of 18th domain by the linker DNA, which preferably comprises the nucleic acid encoded by the amino acid sequence represented by SEQ ID NO: 18. More preferably, the expression vector in the present invention is pYG-hlEGF illustrated in FIG. 1.

As another embodiment, the present invention relates to the host cell transfected with the expression vector.

The host cell is preferably the yeast cell, and more preferably the KEX1 gene deleted yeast cell.

In order to delete the KEX1 gene, any gene deletion methods known in the art can be used without any limitation.

The above described KEX1 gene-deleted yeast cell transfected with the expression vector may secrete a large amount of active hEGF out of the cell.

The description of the yeast is as aforementioned.

Effect of Invention

According to the present invention, hEGF with the same size and activity as wild type hEGF can be produced in a large amount and the existing yeast expression system, which has not been widely used in recombinant protein expression due to the low productivity, are improved more efficiently. In addition, when using the method of the present invention, hEGF can be easily produced excessively and used variously for medical purpose, cosmetics, etc.

MODE FOR INVENTION

Hereinafter, the present invention is described in more detail through providing Examples as below. However, these Examples are merely meant to illustrate, but in no way to limit, the claimed invention.

Example 1

Figure 1:
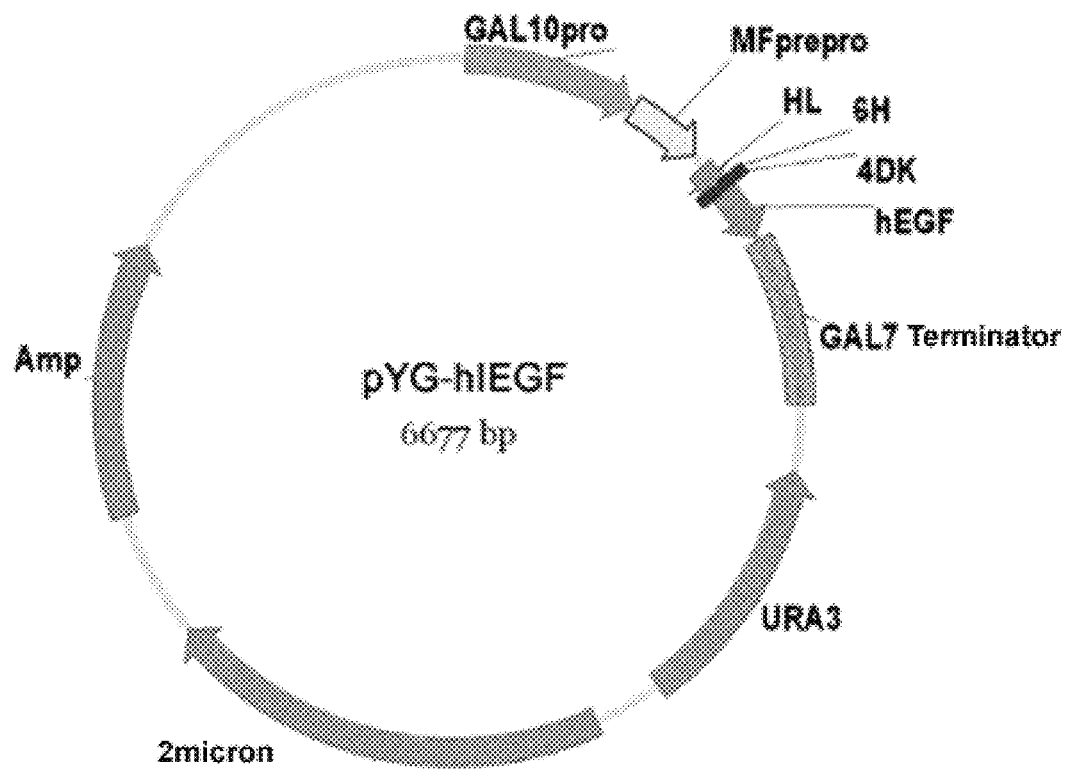
FIG. 1 represents the structure of pYG-hlEGF which is the hEGF expression vector, and the amino acid sequence of HL peptide. Also depicted is SEQ ID NO:19.

Preparation of EGF Expression Strain Using Hydrophilic Domain (HL) of VOA1 (YGR106c) Gene as Secretory Fusion Partner The present inventors identified the C-terminus removed yeast VOA1 (YGR106c) gene to be secreted excessively out of the cells and utilized the same as the secretory fusion partner. In particular, HL peptide (Hydrophilic domain) consisting of amino acid sequence of SEQ ID NO:14, which has the highest charges among the domains of VOA1 protein due to the composition of hydrophilic amino acid, was used as the optimal site of the secretory fusion partner of hEGF (SEQ ID NO:14 VINSLGWAFEDEDGDDEYATEETLS).

pYG-hlEGF, which is the hEGF expression vector, was prepared by fusing hEGF with HL peptide consisting of the amino acid sequence of SEQ ID NO: 14 (FIG. 1). First, HL peptide gene linked to MFα pre-pro leader peptide gene by using GAL100 primer (SEQ ID NO: 1) and DDK-R (SEQ ID NO: 2) was amplified, and hEGF gene was amplified using the sense primer H410 (SEQ ID NO: 3) comprising complementary sequence with DDK-R primer and the hEGF gene sequences, and anti-sense primer H411 (SEQ ID NO: 5) comprising some of GT50R primer (SEQ ID NO: 4) recognizing GAL7 transcription terminator. Polymerase chain reaction (PCR) was performed once for 5 min at 94° C.; 25 times of reaction for 30 seconds at 94° C., for 30 seconds at 55° C., for 3 minutes at 72° C., and for 1 minute at 72° C.; once for 7 minutes at 72° C. Each amplified PCR product was linked to MFα pre-pro leader peptide gene, HL peptide gene and hEGF gene in order by overlap-extension polymerase chain reaction with GAL100/GT50R primer. Using this method, MFα pre-pro leader peptide and HL peptide was linked with linker peptide of AASASAGLALDKR sequence (SEQ ID NO: 18). KR amino acid sequence included in the linker acted as a recognition site of the KEX2 yeast protease and served for separating MFα pre-pro leader peptide from hEGF protein fused with HL peptide in the secretion process. Six histidine amino acid residues were comprised in HL peptide terminus and acted as the affinity markers for purification. In addition, in order to separate HL peptide and hEGF, the DDDDK amino acid sequence (SEQ ID NO: 16), which is recognition site of enterokinase (EK), was added between HL peptide and hEGF. Since EK cuts the carboxy terminus of DDDDK sequence, hEGF protein can be produced in complete form by treating the fusion protein with EK.

The strain transfected with pYG-hlEGF vector was prepared by treating fused gene fragments and pYG-hlEGF vector with EcoRI/SalI, transfecting the resultant to the yeast Y2805 strain with EGF gene deleted vector, and inducing in vivo recombination. Since the yeast *Saccharomyces cerevisiae* has a high recombinant efficiency between homologous genes, simultaneous transfection of the linearized vector and the gene fragment comprising more than 30 bases of identical base sequences at both termini leads to intracellular recombination of the genes in the homologous sites, and the vector in the circular form, wherein the gene fragment and the linearized vector are linked to each other, can be produced. The prepared pYG-hlEGF vector is the sequential linkage of GAL10 promoter, MFα pre-pro leader peptide, linker, HL peptide, 6 histidines, EK cutting sites, hEGF, GAL7 terminator, and therefore the transcriptome generated by strong induction of expression by GAL10 promoter is synthesized in the form of fusion protein of sequential linkage of MFα pre-pro leader peptide, linker, HL peptide, hEGF in the ribosome. Then, when entering the secretory pathway by MFα pre peptide, MFα pre peptide is first removed in the endoplasmic reticulum, and the optimal structure can be formed with the aid of MFα pro peptide and HL peptide. The produced hEGF fusion protein moves to the Golgi apparatus, has MFα pro peptide separated, and then is secreted extracellularly in the form of fusion protein of the linkage only of HL peptide and hEGF.

Example 2

Identification of Increase in hEGF Productivity by HL Peptide

In order to determine the effect of HL peptide consisting of amino acid sequence of SEQ ID NO: 14 on the hEGF productivity, hEGF expression vector linked directly to MFα pre-pro peptide without the HL peptide was prepared by the same method as Example 1. The amount of secreted hEGF and HL-hEGF fusion proteins were compared after culturing the transfected yeast strains with YgaMF-EFG vector and pYG-hlEGF vector in vitro. After culturing each strain in a test tube containing YPDG medium (yeast extract fluid 1%, peptone 2%, glucose 1%, and galactose 1%) for 40 hours at 30° C., acetone of 0.4 ml was added to the culture fluid of 0.6 ml and precipitated. The resultant was dissolved in a buffer, and then the size and the amount of secreted proteins were compared by SDS-PAGE analysis.

Figure 2:
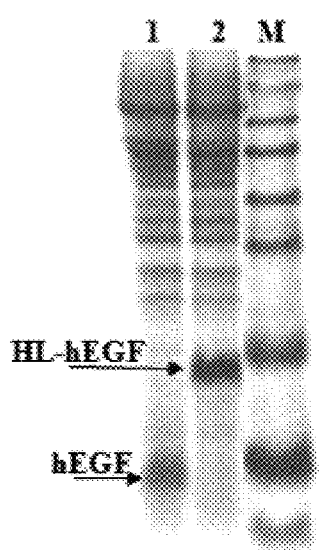
FIG. 2 is the comparison of the hEGF productivity of the yeasts transfected with YGaMF-EGF and pYG-hlEGF vectors (lane 1: YGaMF-EGF expression strain supernatant, lane 2: pYG-hlEGF expression strain supernatant, Lane M: protein size markers).

As a result, the expression level of hEGF, when expressed in the form of HL-hEGF fusion protein (lane 2), was identified to increase by about 5 times compared to the case of the production through sole secretion (lane 1) (FIG. 2).

Example 3

Fermentation and Purification for Producing hEGF

In order to determine the hEGF productivity of the strain transfected with pYG-hlEGF identified in Example 2, fed batch fermentation and culture were performed using the same strain. The strains cultured in the minimal medium of 200 ml were inoculated to the fermentor of 5 L scale containing 1.8 L fermentation medium (2% glucose, 4% yeast extract, 1% peptone). When the glucose is completely exhausted, fermentation can proceed for 50 hours while adding feed medium (30% glucose, 30% galactose, 15% yeast extract) gradually by 2 g/L to 20 g/L per hour, depending on the growth of the cell.

Figure 3:
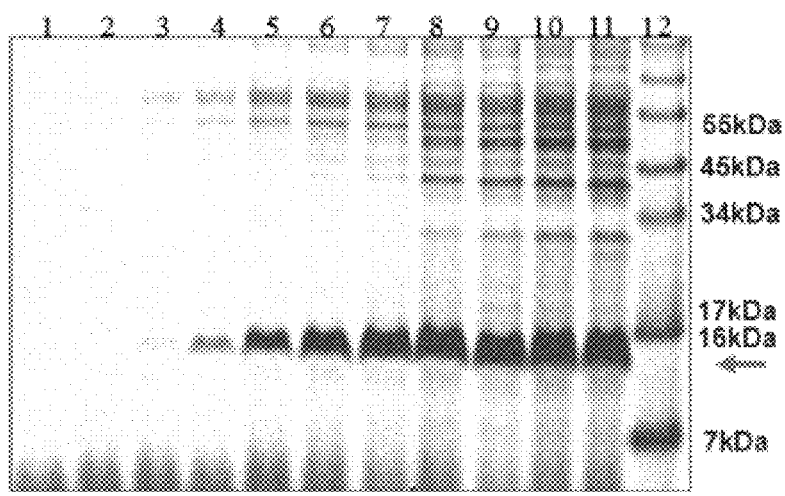
FIG. 3 is the results of SDS-PAGE analysis of the supernatant after fermentation of the yeast transfected with pYG-hlEGF vector (lane 1-11: fermentation supernatant, lane 12: protein size markers).

As shown in FIG. 3, the result of direct SDS-PAGE analysis of 10 μl fermentation medium without concentration identified that the fusion protein is secreted approximately more than 500 mg/L at the end of fermentation.

In order to purify the hEGF fusion protein secreted into the fermentation medium, the fermentation medium was concentrated by 5 times with 30,000 MWCO Quick-stand (Amersham-Pharmacia Biotech, N.J.) after the first purification using a filter (Satorious), and the composition of concentrate was adjusted to 50 mM Tris-Cl (pH8.0), 0.5M NaCl in the concentration process in order to be immediately applied to Ni-NTA column. Fusion protein was combined to Ni-NTA resin by applying the fermented concentrate of 50 ml to Ni-NTA column of 20 ml, and HL-hEGF fusion protein was purified by flowing 50 mM Tris-HCl (pH 8.0), 0.5 M NaCl, 0.5 M imidazole solution with concentration gradient using MPLC (Medium Pressure Liquid Chromatography, Bio-rad). In order to remove HL peptide from the purified fusion protein, the composition of the purified solution was adjusted to 20 mM Tric-HCl (pH 8.0), 50 mM NaCl, and 2 mM $CaCl_2$, which is the operation condition of enterokinase (EK), using 5,000 MWCO Amicon Ultra centrifugal filter device (Millipore). Fusion protein of 1 μg was treated with EK of 1 unit at 16° C. for over 15 hours. EK-treated protein was purified again using MPLC and Ni-NTA column by the same method as the above.

Figure 4:
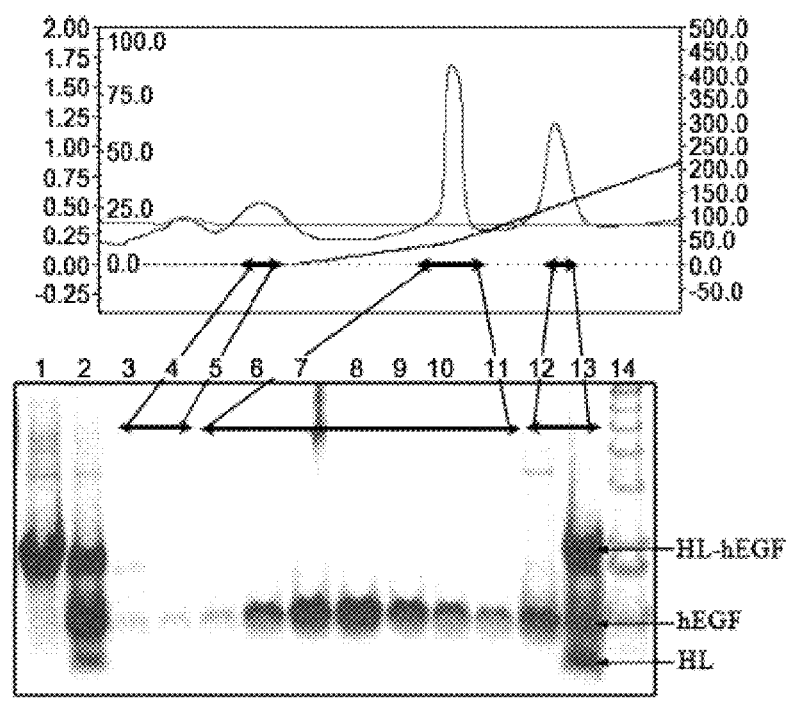
FIG. 4 is the result of fermenting yeast transfected with pYG-hlEGF vector, purifying the supernatant, removing HL peptide, and then purifying the pure hEGF. The figure on the top is MPLC chromatogram, and the figure at the bottom is the result of SDS-PAGE analysis of the fraction corresponding to the peak on the chromatogram (lane 1: purified HL-hEGF fusion protein, lane 2: EK-treated HL-hEGF fusion protein, lanes 3-13: fraction of EK-treated HL-hEGF fusion proteins separated by MPLC, lane 14: protein size markers).

As a result, hEGF protein with high purity, as shown in FIG. 4, was purified.

Example 4

Preparation of KEX1 Gene-Deleted Yeast Strain for Producing Active hEFG

In order to identify the hEGF protein purified in Example 3, the sequence of the amino terminus and the molecular weight were measured (Korea Basic Science Institute). The amino acid sequence of the amino terminus was perfectly identical to that of hEGF, but the molecular weight was identified to be 6,064 Da, which is smaller than the molecular weight of 6,214 Da of the hEGF protein in the complete form composed of the 53 amino acids. The molecular weight of 6,064 Da is identical in the magnitude with that of hEGF composed of 52 amino acids, from which one lysine amino acid at the carboxy terminus is removed. Assuming that the truncation of the carboxy terminus of hEGF can happen by the action of the KEX1 protease, the KEX1 gene deleted strain was prepared.

Deletion of KEX1 gene was performed using URA3 popout vector.

Figure 5:
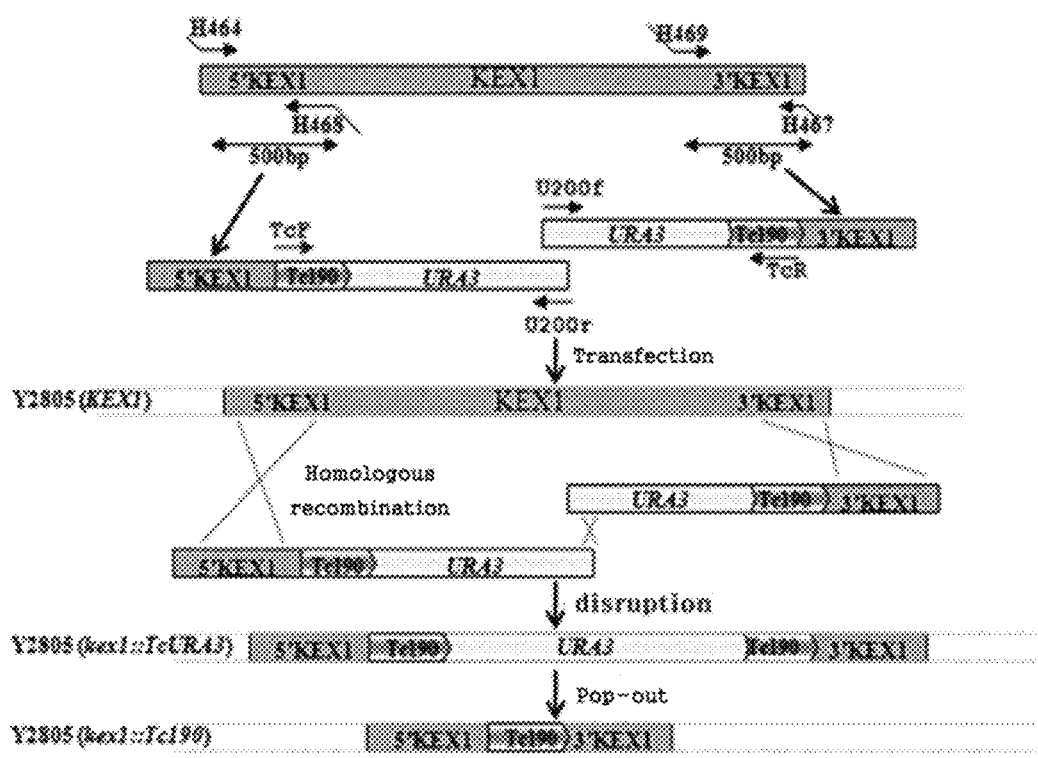
FIG. 5 represents the preparation process of the KEX1 gene-deleted strain.

First, the primer H464 (SEQ ID NO: 6)/H468 (SEQ ID NO: 7), H469 (SEQ ID NO: 8)/H467 (SEQ ID NO: 9) was used for 5' region 500 bp and 3' region 500 bp of KEX1 gene, each was amplified by performing polymerase chain reaction (PCR) once for 5 minutes at 94° C.; 25 times of reaction for 30 seconds at 94° C., for 30 seconds at 55° C., for 3 minutes at 72° C., and for 1 minutes at 72° C.; once for 7 minutes at 72° C., and URA3 pop-out cassette was divided to TcF (SEQ ID NO: 10)/U200R (SEQ ID NO: 11), and U200F (SEQ ID NO: 12)/TcR (SEQ ID NO: 13), using pTcURA vector as a template, each of which was amplified (FIG. 5). 5' region 500 bp of KEX1 gene was linked to 5' region of cassette amplified by primer TcF/U200R as one fragment by performing overlap extension polymerase chain reaction using the primer set H464/U200R. H468 primer comprises the complementary sequence to TCF primer and therefore two fragments can be linked as one fragment by PCR. In the same way, 3' region 500 bp of KEX1 gene was linked to 3' region of cassette amplified by primer U200F/TcR as one fragment using the primer set U200F/H467. The linked fragment was transfected to the yeast *Saccharomyces cerevisiae* Y2805 (Mat a ura3 INV2 pep4::HIS3) strain and the transformant Y2805Δkex (Mat a kex1::Tc190URA3 pep4::HIS3) was screened in a selective medium without uracil. In order to remove URA3 gene inserted into KEX1 gene and reuse URA3 gene as a selectable marker, the strain was cultured in fluoroorotic acid (5-fluoroorotic acid, 5-FOA) medium and the strain Y2805Δkex (Mat a, ura3, kex1::Tc190 pep4::HIS3) which URA3 gene popped out from was selected. It was confirmed through PCR that the KEX1 gene on chromosome was deleted as expected and URA3 gene popped out again.

Example 5

Production of hEGF Using the KEX1 Gene-Deleted Strain and Analysis of hEGF Activity After hEGF expression strain was produced by transfecting pYG-hlEGF vector prepared in Example 1 to the KEX1 gene-deleted strain produced in Example 4, fermentation and purification were carried out by the same method as Example 3.

Figure 6:
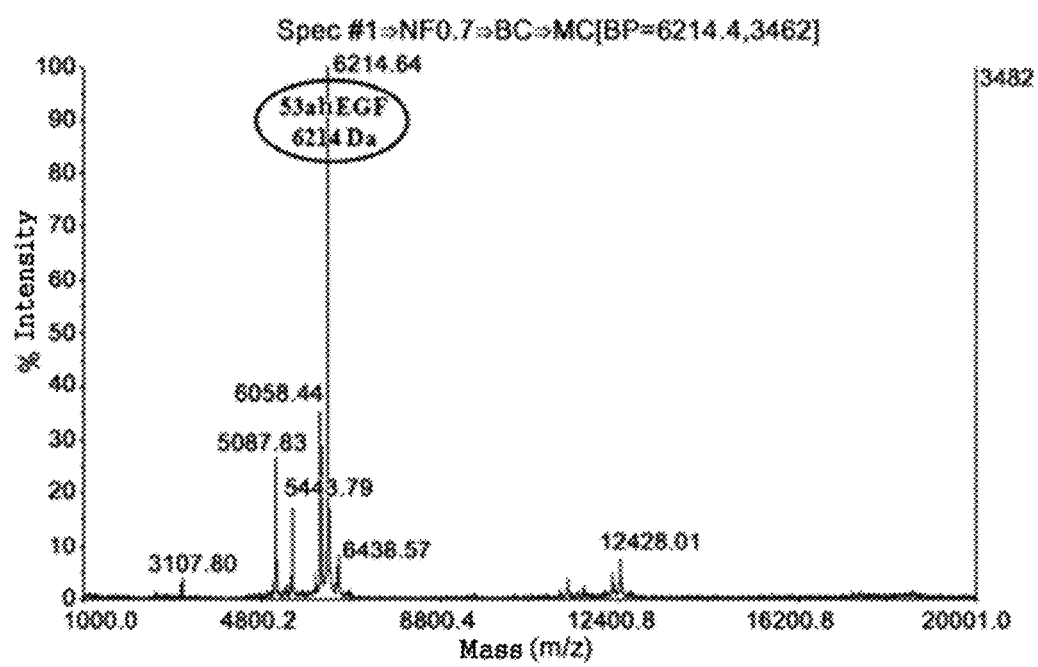
FIG. 6 represents the measurement results of molecular weight of hEGF protein purified by the method of the present invention.
Figure 7:
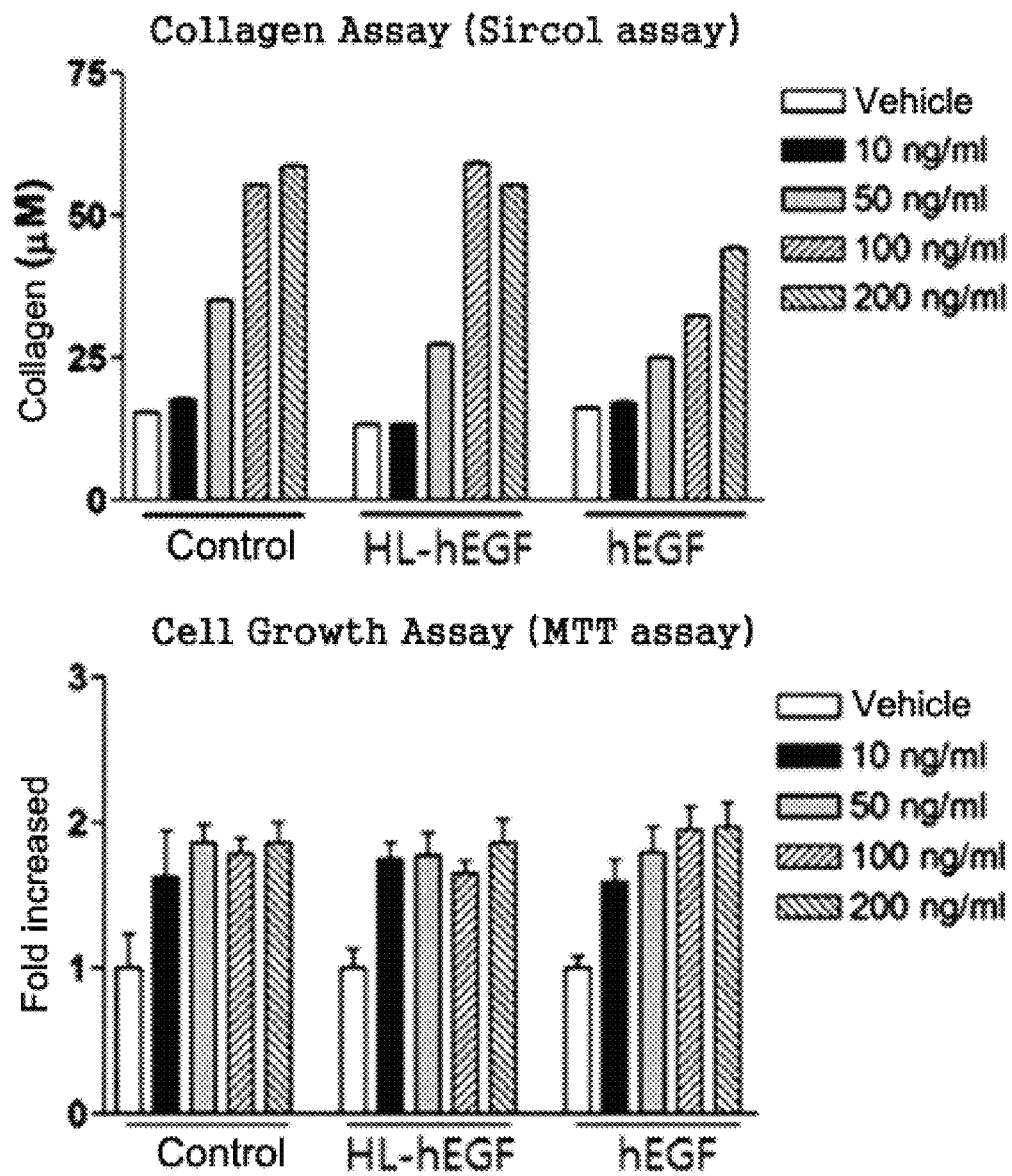
FIG. 7 is the analysis of activity to promote cell growth and collagen synthesis of hEGF and HL-hEGF purified by the method of the present invention.

The production of recombinant proteins in protease-deficient strain typically tend to reduce the productivity of recombinant proteins, but in the present invention, the KEX1 gene deleted strain and wild-type strain didn't show the difference in hEGF productivity. As a measurement result of molecular weight by a researcher in Korea Basic Science Institute commissioned for the qualitative analysis of purified hEGF protein, hEGF protein has the size of 6064 Da consisting of 52 amino acids in the wild type strain, but most has the complete size of 6221 Da consisting of 53 amino acids in the KEX1 gene deleted strain (FIG. 6). In order to analyze the activity of the produced yeast-derived hEGF, HL fused hEGF (HL-hEGF) and HL removed hEGF (hEGF), which are two types of purified hEGFs, are commissioned to Skin Biotechnology Center, Kyung Hee University, to analyze the promotion of cell growth (MTT assay) and collagen synthesis (FIG. 7). As shown in the results, both types of purified protein exhibited similar activity as commercialized, purified EGF and therefore both hEGF and HL-hEGF produced through secretion from yeast were identified to be produced in the active form.

INDUSTRIAL APPLICABILITY

The method of the present invention can produce a large amount of the active form of hEGF, and hEGF produced by the method can be used for medications such wound healing drugs or cosmetics.

What is claimed is:

1. A method for producing human epidermal growth factor (hEGF) comprising: i) preparing an expression vector encoding an hEGF fusion protein comprising a polypeptide sequence of SEQ ID NO: 14 fused directly to the N-terminus of the hEGF polypeptide; ii) transfecting a KEX1 gene-deleted yeast host cell with said expression vector; iii) culturing said yeast host cell to produce the fusion protein; and iv) purifying the fusion protein from the culture.

2. A method for producing human epidermal growth factor (hEGF) comprising: i) preparing an expression vector encoding an hEGF fusion protein comprising the polypeptide sequence of SEQ ID NO: 14 fused directly to an affinity tag wherein the C-terminus of the affinity tag is fused to the hEGF polypeptide; ii) transfecting a KEX1 gene-deleted yeast host cell with said expression vector; iii) culturing said yeast host cell to produce the fusion protein; and iv) purifying the fusion protein from the culture.

3. A method for producing human epidermal growth factor (hEGF) comprising: i) preparing an expression vector encoding an hEGF fusion protein comprising the polypeptide sequence of SEQ ID NO: 14 fused directly to an affinity tag wherein the C-terminus of the affinity tag is fused to a protease recognition sequence and wherein the C-terminus of the protease recognition sequence is fused to the hEGF polypeptide; ii) transfecting a KEX1 gene-deleted yeast host cell with said expression vector; iii) culturing said yeast host cell to produce the fusion protein; and iv) purifying the fusion protein from the culture.

4. The method according to any one of claims 1-3, wherein the hEGF comprises the amino acid sequence of SEQ ID NO: 15.

5. The method according to any one of claims 2-3, wherein the affinity tag is selected from the group consisting of GST, MBP, NusA, thioredoxin, ubiquitin, FLAG, BAP, 6HIS, STREP, CBP, CBD, and S-tag.

6. The method according to claim 3, wherein the protease recognition sequence is selected from the group consisting of yeast kex2p-recognition sequence, mammalian purine-recognition sequence, Factor Xa-recognition sequence, enterokinase-recognition sequence, subtilisin-recognition sequence, tobacco etch virus protease-recognition sequence, thrombin-recognition sequence, and ubiquitin hydrolase-recognition sequence.

7. The method according to claim 6, wherein the protease recognition sequence is enterokinase-recognition sequence.

8. The method according to claim 7, wherein the affinity tag is 6HIS.

9. The method according to claim 7 or 8, further comprising treating the fusion protein with enterokinase.

10. The method according to any one of claims 1-3, wherein the yeast host cell is selected from the group consisting of candida, debaryomyces, hansenula, kluyveromyces, pichia, schizosaccharomyces, yarrowia, saccharomyces, schwanniomyces and arxula species.

11. The method according to claim 10, wherein the yeast host cell is selected from the group consisting of *Candida utilis, Candida boidinii, Candida albicans, Kluyveromyces lactis, Pichia pastoris, Pichia stipitis, Schizosaccharomyces pombe, Saccharomyces cerevisiae, Hansenula polymorpha, Yarrowia lipolytica, Schwanniomyces occidentalis* and *Arxula adeninivorans*.

12. An expression vector encoding a human epidermal growth factor (hEGF) fusion protein, wherein the hEGF fusion protein is selected from the group consisting of:
    (a) a hEGF fusion protein comprising a polypeptide sequence of SEQ ID NO: 14 fused directly to the N-terminus of the hEGF polypeptide;
    (b) a hEGF fusion protein comprising the polypeptide sequence of SEQ ID NO: 14 fused directly to an affinity tag where the C-terminus of the affinity tag is fused to the hEGF polypeptide; and
    (c) a hEGF fusion protein comprising the polypeptide sequence of SEQ ID NO: 14 fused directly to an affinity tag where the C-terminus of the affinity tag is fused to a protease recognition sequence and where the C-terminus of the protease recognition sequence is fused to the hEGF polypeptide.

13. A yeast host cell transfected with the expression vector of claim 12.

14. The host cell according to claim 13, which is a KEX1 gene-deleted yeast.

* * * * *